(12) United States Patent
Scholten et al.

(10) Patent No.: US 12,109,002 B2
(45) Date of Patent: Oct. 8, 2024

(54) MOUNTING ADAPTER FOR SECURING A STERILE COVER ON A MICROSCOPE, MICROSCOPE FOR USE WITH AN ADAPTER OF THIS TYPE, AND SYSTEM HAVING A MICROSCOPE OF THIS TYPE AND AN ADAPTER OF THIS TYPE

(71) Applicant: Digital Surgery Systems, Inc., Goleta, CA (US)

(72) Inventors: Thomas Scholten, Tuttlingen (DE); Klaus-Dieter Steinhilper, Tuttlingen (DE); Marc Delle, Rottweil (DE)

(73) Assignee: Digital Surgery Systems, Inc., Goleta, CA (US)

( * ) Notice: Subject to any disclaimer, the term of this patent is extended or adjusted under 35 U.S.C. 154(b) by 908 days.

(21) Appl. No.: 17/041,031

(22) PCT Filed: Mar. 26, 2019

(86) PCT No.: PCT/EP2019/057611
§ 371 (c)(1),
(2) Date: Sep. 24, 2020

(87) PCT Pub. No.: WO2019/185640
PCT Pub. Date: Oct. 3, 2019

(65) Prior Publication Data
US 2021/0137626 A1 May 13, 2021

(30) Foreign Application Priority Data
Mar. 28, 2018 (DE) .................... 10 2018 107 357.7

(51) Int. Cl.
*A61B 46/10* (2016.01)
*A61B 90/25* (2016.01)
*G02B 21/02* (2006.01)

(52) U.S. Cl.
CPC .............. *A61B 46/10* (2016.02); *A61B 90/25* (2016.02); *G02B 21/02* (2013.01)

(58) Field of Classification Search
CPC ...... A61B 46/10; A61B 90/20; G02B 21/0012
See application file for complete search history.

(56) References Cited

U.S. PATENT DOCUMENTS

| | | | | |
|---|---|---|---|---|
| 3,528,720 A | * | 9/1970 | Treace | A61B 46/10 206/316.1 |
| 3,796,477 A | * | 3/1974 | Geraci | A61B 46/10 359/600 |

(Continued)

FOREIGN PATENT DOCUMENTS

| | | | |
|---|---|---|---|
| CN | 110082899 A | * | 8/2019 |
| CN | 209347248 U | * | 9/2019 |

(Continued)

OTHER PUBLICATIONS

Written Opinion of the International Searching Authority received in Application No. PCT/EP2019/057611, 13 pages.

(Continued)

*Primary Examiner* — Christopher Stanford
(74) *Attorney, Agent, or Firm* — K&L Gates LLP; Dennis A. Majewski

(57) ABSTRACT

A mounting adapter for detachably attaching a sterile cover to an objective of a microscope includes a passage for inserting the objective. A drape-lens or light-transparent disc is arranged in the passage such that it adopts an oblique angle to the longitudinal axis of the passage. The mounting adapter includes a latching device for an axially holding of the mounting adapter on the objective inserted into the passage. A positioning geometry causes a reproducible target angular positioning or target rotational alignment of the mounting adapter on the objective by its axial attachment to (Continued)

fulfil its positioning function independently and separately from the latching device.

10 Claims, 8 Drawing Sheets

(56) References Cited

U.S. PATENT DOCUMENTS

| | | | | |
|---|---|---|---|---|
| 4,266,663 | A * | 5/1981 | Geraci | A61B 46/10 |
| | | | | 206/316.1 |
| 4,385,812 | A * | 5/1983 | Wille | A61B 46/10 |
| | | | | 359/511 |
| 4,561,540 | A * | 12/1985 | Hunter | G02B 21/0012 |
| | | | | 383/71 |
| 4,564,270 | A * | 1/1986 | Willie | A61B 46/10 |
| | | | | 359/511 |
| 4,723,912 | A * | 2/1988 | Nieusma | A61C 1/16 |
| | | | | 433/116 |
| 4,799,779 | A * | 1/1989 | Mesmer | G02B 21/0012 |
| | | | | 206/316.1 |
| 5,155,624 | A * | 10/1992 | Flagler | G02B 21/00 |
| | | | | 359/511 |
| 5,311,358 | A * | 5/1994 | Pederson | G02B 21/00 |
| | | | | 359/511 |
| 5,467,223 | A * | 11/1995 | Cleveland, Jr. | G02B 21/0012 |
| | | | | 359/511 |
| 5,608,574 | A | 3/1997 | Heinrich | |
| 5,682,264 | A * | 10/1997 | Cleveland | G02B 21/24 |
| | | | | 359/511 |
| 5,772,355 | A * | 6/1998 | Ross | G02B 23/2484 |
| | | | | 403/321 |
| 5,792,045 | A * | 8/1998 | Adair | A61B 1/00128 |
| | | | | 600/125 |
| 6,024,454 | A * | 2/2000 | Horan | A61B 46/10 |
| | | | | 359/511 |
| 6,116,741 | A * | 9/2000 | Paschal | A61B 46/10 |
| | | | | 359/511 |
| 6,257,730 | B1 * | 7/2001 | Kleinberg | G02B 21/24 |
| | | | | 359/600 |
| 6,876,503 | B1 * | 4/2005 | Weaver | G02B 21/0012 |
| | | | | 359/818 |
| 7,232,230 | B2 * | 6/2007 | Bala | G02B 7/001 |
| | | | | 359/510 |
| 8,506,094 | B2 * | 8/2013 | Chua | G02B 27/0006 |
| | | | | 359/511 |
| 9,795,279 | B2 * | 10/2017 | Hogrefe | A61B 1/00126 |
| 10,156,718 | B2 * | 12/2018 | Koenig | G02B 27/0006 |
| 11,493,755 | B2 * | 11/2022 | Yamane | G02B 27/0006 |
| 2005/0094269 | A1 * | 5/2005 | Moses | A61B 46/10 |
| | | | | 359/507 |
| 2007/0064309 | A1 * | 3/2007 | Luloh | A61B 46/10 |
| | | | | 359/507 |
| 2008/0144178 | A1 * | 6/2008 | Dillon | A61B 46/10 |
| | | | | 359/510 |
| 2010/0238551 | A1 * | 9/2010 | Hubbs | G02B 27/0018 |
| | | | | 359/601 |
| 2017/0168292 | A1 | 6/2017 | Koenig et al. | |
| 2021/0137626 | A1 * | 5/2021 | Scholten | A61B 46/10 |

FOREIGN PATENT DOCUMENTS

| | | | | |
|---|---|---|---|---|
| CN | 110353829 A | * | 10/2019 | ......... A61B 1/00147 |
| DE | 29712376 U1 | | 11/1998 | |
| DE | 202021103006 U1 | * | 7/2021 | ............ A61B 46/10 |
| EP | 3178438 A1 | | 6/2017 | |
| WO | WO-2009037193 A2 | * | 3/2009 | ............ A61B 46/10 |

OTHER PUBLICATIONS

German Search Report received in Application No. 102018107357.7 dated Nov. 9, 2018, 16 pages.

International Search Report received in Application No. PCT/EP2019/057611 dated Jun. 19, 2019, 2 pages.

* cited by examiner

MOUNTING ADAPTER FOR SECURING A STERILE COVER ON A MICROSCOPE, MICROSCOPE FOR USE WITH AN ADAPTER OF THIS TYPE, AND SYSTEM HAVING A MICROSCOPE OF THIS TYPE AND AN ADAPTER OF THIS TYPE

CROSS-REFERENCE TO RELATED APPLICATIONS

This application is the United States national phase of International Application Number PCT/EP2019/057611, filed Mar. 26, 2019, which claims the benefit of priority of German Application No. 10 2018 107 357.7, filed Mar. 28, 2018. The contents of International Application Number PCT/EP2019/057611 and German Application No. 10 2018 107 357.7 are incorporated by reference herein.

FIELD

The present invention relates to a mounting adapter, hereinafter referred to as an adapter, for detachably attaching a defined recess of a sterile cover to an objective of a microscope, in particular a surgical microscope which allows a quick and easy mounting in only one single mounting position and still ensures a secure attachment of the sterile cover to the microscope. Furthermore, the invention concerns a system comprising a surgical microscope and such an adapter.

BACKGROUND

In modern surgery, surgical microscopes which allow a surgeon or surgeons to have a better view of the operating field are being increasingly used. However, since such microscopes cannot be sterilized before an operation like other surgical instruments, surgical microscopes must be covered or wrapped in a sterile cover before an operation to prevent contamination during the operation due to the non-sterile microscope itself. Such sterile covers are also known as "drapes". Thereby, such a sterile cover allows indeed sterile working, but does not have a negative effect on the image quality, the sterile cover must be closed in the area of the objective of the microscope, but must have a light-transmissive recess or window (also known as a "drape-lens"), which allows the passage of beam, especially light beams. In order to optimally illuminate the surgical field optimally, the light emitted for illumination must follow a path similar to that of the light returning into the microscope along the optical axis. In this case the light emitted for illumination must be guided in such a way that unwanted reflections, e.g. a mirror image of the light source, do not occur in the area of the operating field.

One possibility to greatly reduce reflections is to provide the light transmissive recess or window in the sterile cover or the "drape-lens" and/or surrounding geometries provided with a coating that reduces reflections.

Another possibility is to arrange the drape-lens at a defined acute angle to the optical lens, i.e. at an angle that differs significantly from a right angle.

The positioning and mounting of the drape-lens on the objective of the surgical microscope is realized by means of an adapter which holds or fixes the drape-lens in a predetermined and reproducible position with respect to the objective of the microscope. Thus, the adapter also determines the angular position of the drape-lens with respect to the optical axis.

The applicant of the present invention has stated that the exact positioning of the adapter on the objective of the microscope thus requires the exact positioning of the drape-lens in a target relative position with respect to the optical axis, which is decisive for ensuring a consistently high image quality. If the adapter is mounted incorrectly on the objective of the microscope, for example, mounted twistedly or tiltedly, reflections which impair the image quality may get into the beam path. If the adapter is not fitted firmly enough on the objective of the microscope, the positioning of the adapter may also change over time, which can lead to the decrease in image quality during an operation. Finally, the mounting of the adapter should also be as simple as possible for good handling and user-friendliness. Various adapters for detachable attachment of a drape-lens and a drape to a surgical microscope are known from the state of the art.

For example, some adapters use an elastic form fit, for example in the form of a rubber band or a rubber sleeve between the adapter and the surgical microscope, to attach the adapter to the microscope.

Often the microscope has on its outer surface form elements/contours which are undercut by corresponding form elements of the adapter. For example, the inner circumference of the adapter can be stretched or deformed and applied to the microscope in this state. The user then releases the adapter which is then elastically deformed back into its initial configuration and held on the microscope by the undercutting form elements.

However, such an elastic form fit has the disadvantage that either the user has to apply a high force when mounting the adapter on the microscope, e.g. when a large deformation of the adapter or the undercutting elements is required to apply the adapter on the microscope, or there is an increased probability of an unwanted disassembly of the adapter from the microscope, e.g. when there is only a slight oversize of the undercutting elements. In addition, the adapter cannot be mounted in a single desired and reproducible mounting position but can be attached on the objective in a twisted or tilted way.

Another adapter known from the state of the art is substantially an elastomeric element with an inserted drape-lens. The adapter can be attached on the objective of a microscope in an axial direction in the manner of a wide rubber ring. The mounting of the adapter is simple and the number of components of the adapter is small.

In addition to the problems of such an elastic form fit described above, namely an increased required mounting force in case of a large oversize and an increased probability of unwanted disassembly in case of a small oversize, the adapter can also be mounted not only in one single desired mounting position, but can be attached to the objective in a twisted or tilted way.

Moreover, document U.S. Pat. No. 5,608,574 discloses an adapter which is held frictionally on the objective of a microscope by means of several ribs. Mounting the adapter on the objective is simple, but even with this adapter no reproducible single mounting position is given. Rather, the adapter mounted on the objective can be rotated around the objective and only two corresponding markings on the adapter and the objective serve to indicate a target mounting position but not to determine the only possible mounting position.

Another adapter known from the state of the art allows the adapter to be mounted on an objective of a microscope in only one single reproducible mounting position. However, this is achieved by means of a bayonet lock between the objective and the adapter, which requires an increased number of elements and needs a more precise or difficult procedure for mounting, because a rotational movement is needed instead of a simple axial movement (to fit an adapter).

SUMMARY

Based on the prior art described above, the object of the present invention is to provide an adapter for mounting a sterile cover with a drape-lens to a surgical microscope which manages with the smallest possible number of components, but can be mounted reproducibly on an objective of a microscope in a simple way and in a single predetermined mounting position and stays reliably in the mounting position.

The basic idea of the present invention is therefore to provide a (sterile cover-side) mounting adapter (hereinafter adapter) for detachably attaching a sterile cover to an objective of a microscope which is configured with a penetration or through opening (hereinafter passage) for an exclusively axial (i.e. no rotation required) attachment to the microscope or its objective and which has a latching device which is selectively movable into and/or out of the passage or selectively increases and/or reduces the diameter/circumference of the passage, wherein the latching device is provided and configured particularly for coming into undercutting latching engagement with a geometry, e.g. a projection or recess on the sides of the microscope or its objective.

Finally, the adapter has at least one positioning geometry, for example in the form of an asymmetry, in particular, in/at the passage, a clearance/recess or projection which causes a (substantially exact) reproducible (automatic/inevitable) angular positioning or rotational alignment of the adapter on the microscope/objective exclusively when the latter is axially attached. Preferably, the positioning geometry operates independently of the latching device and is further preferably functionally and/or locally divided/separated from the latching device.

In this respect, the adapter according to the invention and the microscope/microscope objective function according to the key-keyhole principle, according to which only one adapter with an individually/generally designed or determined positioning geometry and, if applicable, a preferably individually/generally designed or determined latching device is axially (without necessary rotational movement) mounted on a microscope of a specific type, and thereby, on the one hand, produces the axially securing latching engagement with the microscope/objective and, on the other hand, ensures the relative angular position of the adapter with respect to the microscope/objective.

More concretely, the positioning geometry of the adapter preferably forms at least one alignment receptacle (e.g. axial hole/recess) into which, during mounting of the adapter on the microscope/objective, for example, a corresponding engaging portion, preferably an alignment post or alignment pin or a spring/strip on the objective of the microscope in axial direction when the alignment receptacle and the engaging portion (alignment pin, etc.) substantially overlap/overlap axially while the relative angular position (actual angular position corresponds to a target angular position) of adapter and objective is correct. A microscope according to the invention therefore preferably has such an engaging portion, preferably an alignment post/pin or strip which is designed to engage in the alignment receptacle of the adapter according to the invention when the relative angular position of adapter and objective is correct. By the form fit between the alignment receptacle on the adapter side and the engaging portion on the microscope side (alignment post/pin or strip), the adapter can only be mounted on the objective (by an exclusively axial displacing movement) in preferably a single position (target angular position) and is simultaneously secured against twisting and tilting of the adapter relative to the objective. The latter results particularly from the fact that the positioning geometry (the alignment receptacle) on the adapter is radially spaced from the passage or protrudes radially over the actual circumference of the passage, whereby the microscope/objective or its engaging portion (alignment post/pin or strip) can exert an axially acting support on the adapter.

An adapter according to the invention for detachably attaching a sterile cover to an objective of a microscope, according to a preferred aspect of the present invention, comprises a base plate containing or receiving the transparent window (drape-lens) tilted/adjusted with respect to the base plate, a cap fitted on the base plate and a movable or slidably received/guided element, preferably in the form of a tongue plate, arranged between the base plate and the cap.

The base plate, the cap and if applicable the tongue plate each have, according to a sub-aspect of the present invention, a penetration/through opening which constitutes the common passage, whereby the adapter can be guided/fitted over the objective of a microscope, wherein, by displacing the tongue plate relative to the base plate and cap (and perpendicularly to the through opening), a congruence of the overlapping through openings necessary for the axial placing/inserting to the microscope-objective can be cancelled, in order to thus clamp the microscope-objective in the through openings which are now mutually shifted. In other words, the adapter can comprise two (flatly) to one another fastened plate/frame elements (base plate and cap), each of which has a through opening preferably with substantially the same diameter as one another, wherein a gap/compartment between the plate/frame elements is retained, in which the tongue plate (latching tongue/latch) is movably accommodated, by means of which the through openings in the gap area can be narrowed. The tongue plate (latching tongue/latch) thus forms the latching device according to the invention. It can be configured as a simple latch or as a plate also with a through opening.

In order to ensure correct mounting of the adapter on the objective of a microscope, the adapter according to the invention has the alignment receptacle or positioning receptacle preferably in the form of a hole or a recess on the edge side which is designed to receive a corresponding engaging portion (alignment pin/post or positioning pin/post) of the microscope-objective. The form fit between the alignment receptacle of the adapter and the engaging portion (alignment pin) of the microscope ensures that the adapter can be mounted on the objective in preferably only one single possible mounting position and that always the same mounting position of the adapter on the microscope is achieved when the adapter is repeatedly mounted on the objective. The alignment receptacle thus serves as an anti-twist means and anti-tilt means when mounting the adapter on the microscope.

The adapter according to the invention may be provided with only one single alignment receptacle, or it may also be provided with a plurality of alignment receptacles, each of which interacts with a corresponding engaging portion such as alignment pins or the like geometry on the objective. In the case of a plurality of alignment receptacles, they may all be the same, but alternatively may also differ from one another in their configuration, such as depth, geometry, surface measures. Thus, it is possible to make the adapter universally usable for microscopes of different types with differently arranged/configured engaging portions, where appropriate.

The base plate has preferably a tubular/cylindrical portion or socket which is closed/closable at its one axial end face by an optically transparent element (window) and has an opening with a circumferential flange or collar at its end face facing away from the optically transparent element that eventually forms the base plate. During the usage of the adapter, the cylindrical portion serves preferably to accommodate the objective of a microscope when the adapter is axially mounted on or radially outside the objective. The optically transparent element is the actual window or drape-lens through which the lighting of the operating field and the observation of the operating field is performed. Preferably, a plane of the optically transparent element runs at an acute angle, such as 15-25°, preferably 20°, to a plane of the base plate or particularly the flange/collar forming the base plate.

The cap is preferably attached on the base plate or fitted/placed/fixed/locked thereon and has the above-mentioned through opening which is aligned with the through opening of the cylindrical/tubular portion/body of the base plate and thus forms a common passage with the latter. The cap is preferably arranged or fixed in a fixed relative position with respect to the base plate. The cap can also simply be a plate arranged preferably parallel to the base plate.

At this point, it should be noted that the drape-lens can be provided almost integrally with the base plate, for example by gluing/welding the drape-lens in/on the sockets of the base plate. However, according to an aspect of the present invention, it is also possible to clamp/bias the drape-lens in the socket. The latter can be realized in a simple manner by designing the base plate in two sections, wherein the socket of the base plate forms a projection internally which already defines a corresponding angle of attack/inclination to the longitudinal axis of the socket and serves as a support for the drape-lens. Furthermore, the second section of the base plate which, as the case may be, is locked with the socket can have a pressing portion, for example in the form of pressing legs or a pressing ring which during assembly of the base plate rest against the drape-lens and thereby clamp the already loosely inserted drape-lens between itself and the support. Alternatively, however, it is also possible to configure the cap with a corresponding pressing portion, e.g. in the form of pressing leg or a ring/strip (one-piece material) which during assembly of the base plate and the cap rest against the drape-lens and thus press the drape-lens against the support.

In concrete terms, the drape-lens can be configured with at least one radial projection or a radially extending lug which engages into a cutout on the socket wall formed in the area of the socket-side projection. The pressing portion on the cap then acts on the circumferential portion diametrically opposite to the lug. Since the drape-lens is attached at an oblique angle to the socket axis, the socket length can be selected in such a way that the inserted drape-lens reaches (substantially) one (upper) end face of the socket in the area of the collar surrounding it at its circumferential portion diametrically opposite to the lug. In this way, the pressing portion at the cap formed in this circumferential portion does not have to project into the socket in order to brace the drape-lens between itself and the base plate. Preferably, two diametrically arranged, radially projecting lugs are arranged, one of which engages into the lateral socket cutout immediately above the inner projection on the socket side, wherein the cap acts on the other in a clamping way.

Between the base plate and the cap, as explained above, according to a sub-aspect of the present invention, a kind of insertion slot is formed, into which the movable element/plate latch or the tongue plate (plane-parallel to the cap and/or the base plate) is inserted, which preferably also has a through opening that can be aligned paraxially with the through opening of the cap and the through opening of the cylindrical body/socket of the base plate. In other words, the movable element can preferably be aligned/displaced with the cap and the base plate in such a way that the opening of the movable element, the opening of the cap and the opening of the cylindrical body are congruent and jointly form a common passage.

The movable element can be movable relative to the base plate and the cap in such a way that it can be brought reversibly from a predetermined open state, in which the movable element does not influence the diameter of the passage (i.e. is congruent with the other openings), preferably by a spring tension into a predetermined locking state, in which the movable element reduces the diameter of the passage in a predetermined way (displaced paraxially). For example, the movable element can be displaced between the base plate and the cap in the slot formed therebetween, preferably spring-biasedly, so that it particularly projects into the passage and thus reduces the diameter of the passage in a predetermined manner.

Preferably, the adapter therefore also has at least one biasing element, for example, in the form of a coil spring or compression spring which biases the adapter in the locking state, i.e. biases the tongue plate with respect to the base plate and the cap in a position, in which the through openings are no longer congruent.

In order to attach or mount the adapter on the objective of a microscope, a user can, for example, by applying a pressure/pushing force to the movable element/tongue plate, transfer the movable element from the locking state (not congruently arranged through openings) to the open state (congruently arranged through openings) against the biasing force of the biasing elements. In the open state, according to a preferred aspect of the invention, the common passage is thus maximally opened and the adapter can easily and without much force applied by the user in an axial direction of the objective of a microscope be attached/fitted/slipped to the objective. In doing so, the pin or projection provided on the objective engages positively into the alignment receptacle, preferably formed by a recess or hole on the base plate and/or on the cap, thus ensuring a predefined relative angular position (state/mounting position) between objective and adapter.

When the adapter is in the desired state/mounting position on the objective, the user stops applying the pushing force to the movable element against the spring bias and the at least one biasing element guides the movable element back to the locking position so that the adapter is held on the objective detachably once again when operated again, but in an axially fixed manner in a non-actuated state.

The construction of the adapter according to the invention thus allows a simple and quick mounting, since the adapter does not have to be rotatably attached to the objective by a rotational movement of the user, but the installation is carried out in axial direction, preferably by simply fitting it onto the objective of the microscope.

Preferably, the temporary fixation of the adapter on the objective is achieved by reducing the diameter of the passage in the adapter, preferably by moving the movable element relative to the base plate and/or cap. By reducing the diameter, for example, the objective can be clamped in the adapter by frictional engagement. Alternatively, however, the objective can also have a recess, for example in the form of a circumferential annular groove/slot, in which the movable element engages in the locking position, whereby the adapter is held to the objective by form fit.

At this point, it should be noted that the arrangement of the tongue plate described above is only one possibility for the selective reduction of the passage diameter. Alternatively, a kind of (fan-)rosette or even a simple elastic sealing ring could be arranged. Also, the arrangement of a preferably manually expandable spiral or leg spring would be conceivable.

According to a preferred aspect of the invention, the through opening of the cylindrical body/socket of the base plate and the through opening of the cap are circular in shape and have substantially the same diameter. The through opening of the cylindrical body of the base plate and the through opening of the cap thus form a common diameter of substantially unitary diameter. Preferably, the opening of the movable element has a larger diameter than the openings of the cylindrical body and the cap. However, the opening of the movable element can also have the same diameter as the openings of the cylindrical body and the cap.

The opening of the movable element can be circular in shape. If the opening of the movable element is not circular, it has preferably a rounded or curved outer contour, at least in sections, but preferably less rounded or curved than the respective circular openings of the cylindrical body and the cap, so that a larger effective surface can be provided with the objective than, for example, that of a straight contour.

In order to make it as simple as possible for a user to operate or mount the adaptor, the movable element may have an operating portion, by means of which a user can move the movable element from the predetermined locking state to the predetermined open state, preferably by applying pressure. The operating portion may, for example be ergonomically adjusted to the user's finger or hand and may preferably be configured as a finger recess, to which the user can apply his thumb to exert pressure.

In order that the operating portion and thus the thumb of the user is not obstructive during positioning or mounting the adapter on the microscope, the operating portion according to one aspect of the invention is arranged on the side of the adapter opposite to the alignment receptacle across the passage formed by the openings of the cylindrical body, the cap and the movable element. The arrangement of the alignment receptacle and the operating portion relative to each other thus serves to adjust the adapter ergonomically to the handling of user and to make the assembly of the adapter as simple as possible.

According to another aspect of the invention, the base plate and the cap together form the alignment receptacle (insertion slot). In other words, the base plate and the cap each form a section/section area of the alignment receptacle.

Preferably, the alignment receptacle through the cap extends to the surface of the flange/base plate facing the cap. In other words, the alignment receptacle extends into the body of the adapter formed by the base plate and the cap and is not merely a superficial dent or recess in the surface of the cap. This ensures a secure engagement of the engaging portion (alignment pin or alignment post) in the alignment receptacle.

In order to prevent the movable element from being transferred out of the open state to a position which reduces the diameter of the passage too much, i.e. to a false locking position, the base plate may also have at least one limiting element or stopper, preferably in the form of a projection which limits the movement of the movable element with respect to the cylindrical body and the cap from the predetermined open state to the predetermined locking position. This also prevents the movable element (tongue plate) from accidentally falling out of the insertion slot.

In other words, the movable element can only be moved out of the open state until it comes into contact with the limiting element or stopper and the correct locking position is reached. In other words, for example, the movable element can only be out of the open state towards the passage until it abuts against the limiting element or stopper and is thus stopped in the correct locking position.

A further aspect of the invention relates to a (medical) microscope designed to be used with an adapter according to the invention. Such a microscope has on its objective at least one engaging portion preferably in the form of an alignment pin or an alignment post or a strip or can be equipped/retrofitted with such an engaging portion which is designed to be received in the alignment receptacle of the adapter or to be brought into engagement with the latter, whereby a specific unambiguous mounting position of the adapter on the microscope is determined. The microscope may preferably have a plurality of engaging portions/alignment pins or alignment posts on its objective.

The engaging portion/alignment pin is preferably configured in its dimensions in such a way that it fits (as far as possible) without play in the alignment receptacle of the adapter. The engaging portion/alignment pin is configured to form a form fit with the alignment receptacle or to engage with the alignment receptacle possibly with an undercut. The engaging portion/alignment pin thus serves as protection against twisting and/or tilting of the adapter on the objective.

Another aspect of the invention relates to a system comprising an adapter and a microscope according to the invention, as described above.

BRIEF DESCRIPTION OF THE DRAWING FIGURES

In the following, the preferred embodiments of an adapter according to the invention are described with reference to the drawing figures, of which:

DETAILED DESCRIPTION

Figure 1A:
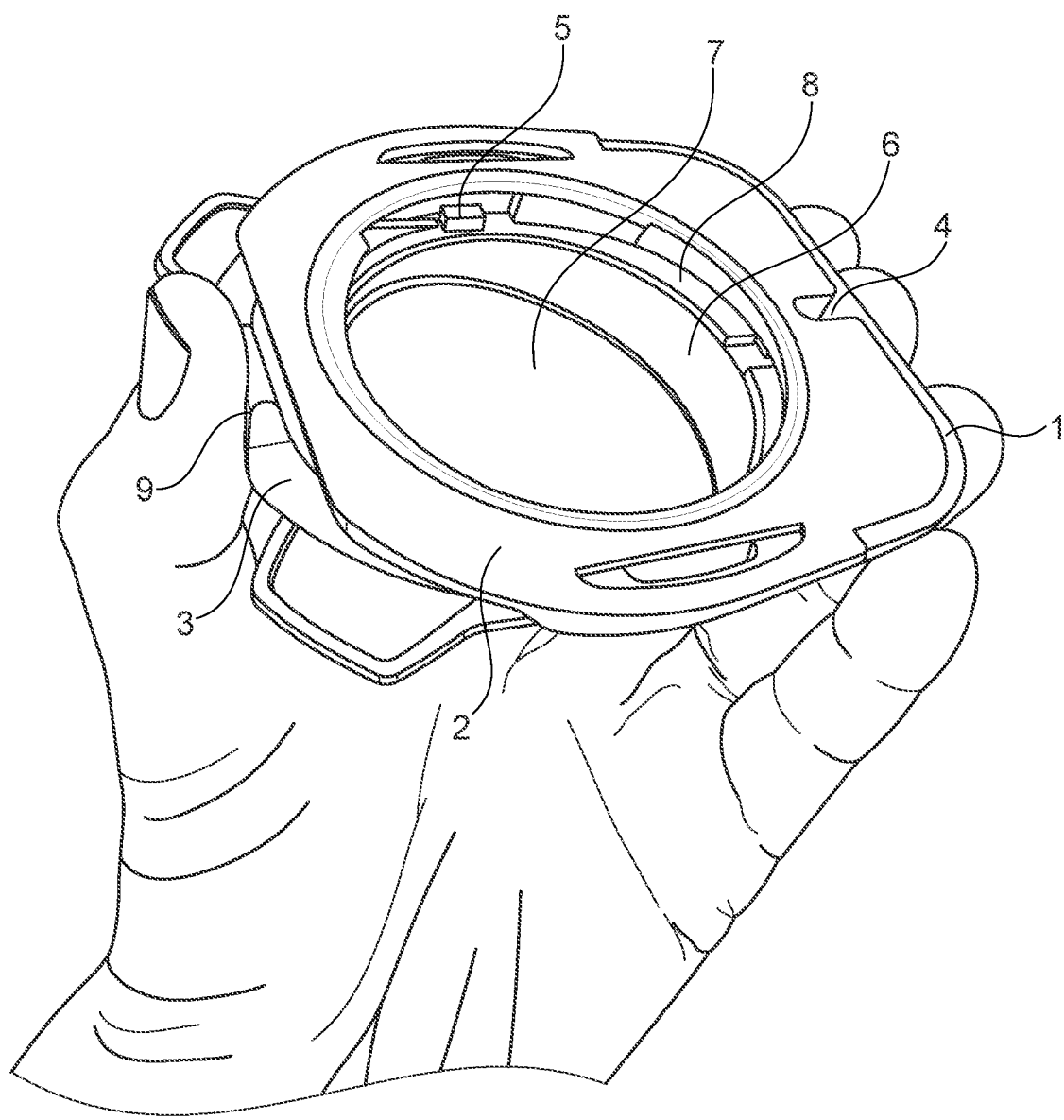
FIG. 1a shows an adapter according to the invention in the open position.

As shown in FIG. 1a, an adapter according to the invention comprises a base plate 1, a cap 2 (flatly) attached thereon and a movable element/tongue plate 3 arranged between the base plate 1 and the cap 2.

The base plate 1 comprises a hollow cylindrical body or socket 6, which is closed at its one (lower) end face by an optically transparent element 7 and which at its (upper) end face facing away from the optically transparent element 7 has an opening 10 with a circumferential flange or collar 8, which forms the base plate 1, wherein preferably one plane of the optically transparent element 7 runs at an (acute) angle of 15°-25°, preferably approx. 20°, to a plane (aligned perpendicular to the socket axis) of the flange 8.

As can be seen particularly in FIGS. 2a to 2c, 3a and 3b, the base plate 1 and the cap 2 each have a (through-) opening 10 and 17, which are coaxially aligned with each other and together form a common passage D. The common passage D can almost be an extension of the cylindrical body 6 of the base plate 1 over the circumferential flange 8. The common passage D thus extends through the openings 10 and 17 of the base plate 1 and the cap 2 to the optically transparent element 7.

Figure 6:
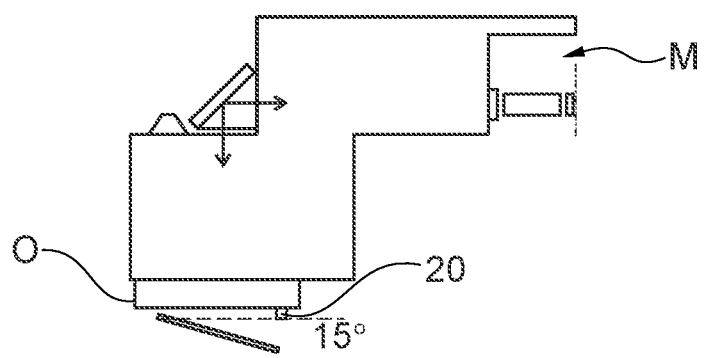
FIG. 6 shows a (medical) microscope with an objective, on which a positioning pin/protrusion is attached or formed.

The movable element 3 also has an opening 18 which can be aligned with the openings 10 or 17 of the cylindrical body 7 of the base plate 1 and the cap 2, so that the openings/all openings 10, 17, 18 of the cylindrical body of the base plate 1, the cap 2 and the movable element 3 are aligned with one another and form the common passage D. The objective O of a microscope M (see FIG. 6) is inserted into the common passage D when the adapter is attached or fitted onto the objective O of the microscope M in an axial direction. In the open position of the adapter, the common passage is therefore opened or has such a diameter that the objective O of the microscope M can be inserted into the adapter.

FIG. 1a further shows a positioning geometry in the form of an alignment receptacle 4, which is preferably formed jointly by the cap 2 and the base plate 1. This alignment receptacle 4 is arranged with a radial distance from the passage D in at least one circumferential portion with respect to the passage.

In the area of the circumferential portion of the adaptor diametrically opposing the alignment receptacle 4, the movable element 3 protrudes beyond the outer edge of the cap 2 and the base plate 1 and has an operating portion 9 in the protruding area, which in the present case is an ergonomic recess, in which a thumb of a user can be placed, as shown in FIG. 1a.

In the depiction shown in FIG. 1a, the user applies pressure with his thumb on the operating portion 9 of the movable element 3. By exerting pressure on the operating portion 9 (thereby pressing the tongue plate against the bias of springs (see FIG. 5b) into a receiving slot between base the plate 1 and the cap 2), the adapter is brought into an open position, in which the movable element does not narrow the passage D.

In the view shown in FIG. 1a, the adaptor is in the open position, in which the diameter of the common passage D is substantially limited only by the dimension of the opening 10 of the cylindrical body 6 of the base plate 1 and the opening 17 of the cap 2. In the open position, the movable element 3 therefore has no influence on the diameter of the common passage D.

In the present invention, the openings 10 and 17 are circular and have substantially the same diameter. In addition, the base plate 1 and the cap 2 are firmly connected to each other, for example by means of latching lugs at the edge side of the base plate 1, which engage/click into undercuts on the edge side of the cap 3, so that the relative positioning of the openings 10, 17 to each other is also fixedly predetermined or unchangeable.

Figure 1B:
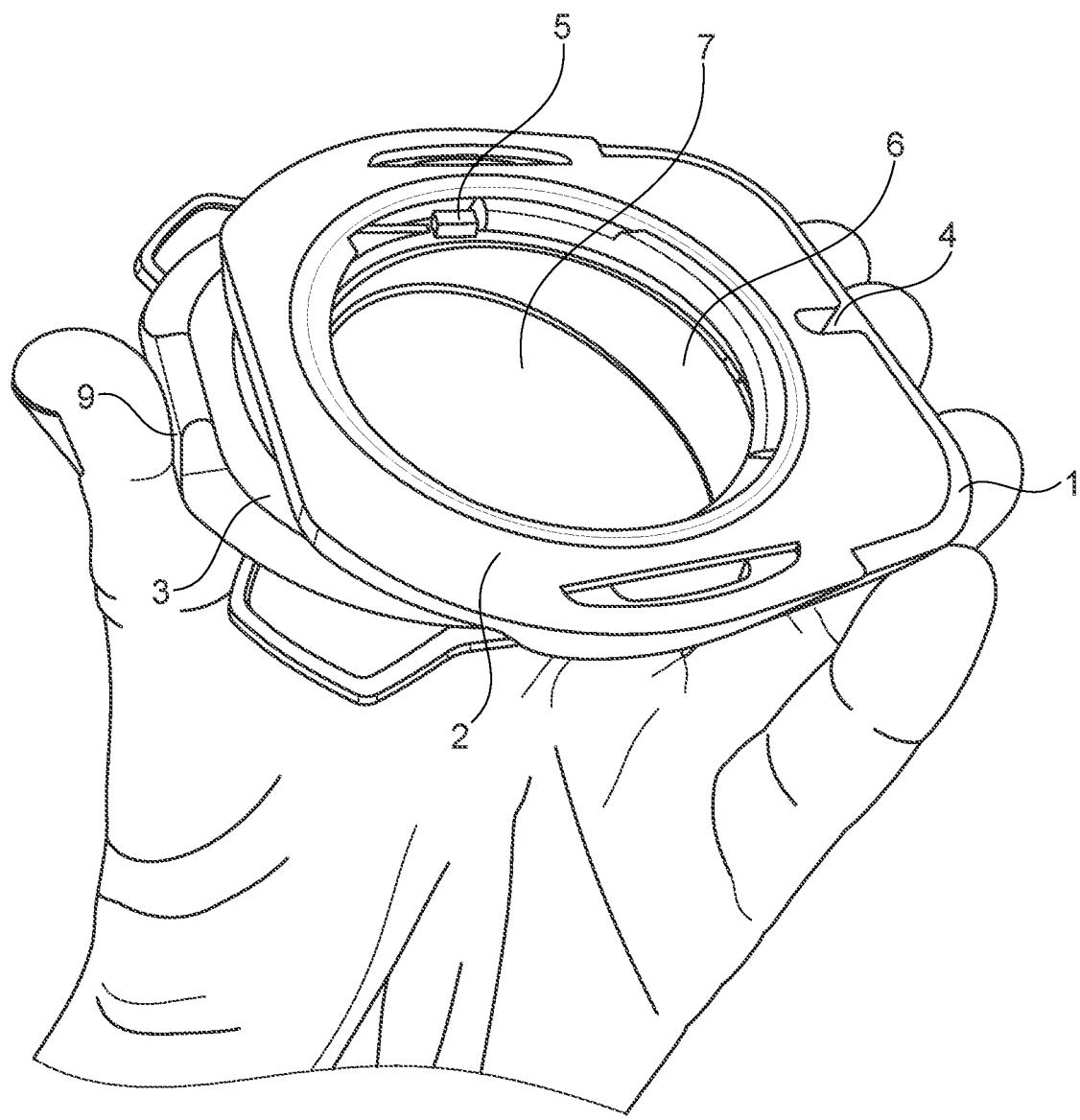
FIG. 1b shows an adaptor according to the invention in the locking position.

FIG. 1a also shows the limiting elements (stoppers) 5 of the base plate 1, which limit the movement of the movable element 3 from the open position shown in FIG. 1a to a locking position shown in FIG. 1b and thus also prevent the movable element 3 from falling out of the insertion slot between the base plate 1 and the cap 2. In other words, the limiting elements 5 limit a movement of the movable element 3, which reduces the diameter of the common passage D or narrows the passage D. In other words, the limiting elements 5 limit a movement of the movable element 3 radially into the passage D. Alternatively or in addition, limiting elements can also be provided at the cap 2 (not shown further).

As can be seen in FIG. 1a, these limiting elements 5 are each configured as a projection or a stopper. In the views shown in FIGS. 1a and 1b, only one such limiting element 5 is visible. In fact, only one such limiting element 5 can be provided in an embodiment of the present invention. Alternatively, several such limiting elements 5 or stoppers may be provided. The limiting elements 5 may be identical or different from each other.

As shown in FIG. 1a, the adaptor according to the invention has the above-mentioned alignment receptacle 4. The adaptor according to the invention may have only one single alignment receptacle 4, but several alignment receptacles 4 of identical or different shape/dimensions may also be provided in different circumferential portions with respect to the passage 4.

FIG. 1b shows the adapter according to the invention in a locking position. As shown in this figure, in the locking position, the movable element 3 projects radially, at least in portions, into the passage D formed by the openings 10, 17 of the cylindrical body of the base plate 1 and the cap 2, thus narrowing the opening of the passage D. When the adapter is mounted on an objective O of a microscope M, the movable element 3 projecting into the passage D undercuts, for example, an annular projection of the objective O, which is not further shown, thereby axially holding the adapter on the objective.

As also clearly shown in FIG. 1b, in the locking position, the movable element 3 preferably abuts against the limiting element 5, that is, it is in contact with the limiting element 5 which therefore limits a movement of the movable element 3 in the direction from the open position to the locking position, which in FIG. 1b corresponds to the direction towards the left.

Furthermore, as shown in FIG. 1b, in the locking position, a user does not have to apply pressure with his thumb on the operating portion 9 of the movable element 3 of the adaptor. When no pressure is applied to the operating portion 9 of the movable element 3, the biasing elements or return elements, which are configured as e.g. coil spring or compression spring as shown in FIG. 5b and are arranged between the movable element 3 and the base plate 1 and/or the cap 2, automatically transfer the movable element 3 from the open position to the locking position.

For mounting the adapter on the objective of the microscope, this means that while pressure is applied to the operating portion 9 of the movable element 3 (i.e. the adapter is in the open position), the adapter is fitted or attached onto the objective along the axial direction of the objective O.

When the adapter is correctly positioned on the objective O, no more pressure is applied to the operating portion 9 of the movable element 3 (the user stops pressing the operating portion 9 of the movable element). The biasing elements or return elements then transfer the adapter to the locking position by moving the movable element 3, so that the diameter of the passage D through the movable element 3 projecting thereinto is reduced, thereby securely anchoring the adapter to the objective of the microscope. In the locking position, the adapter is thus detachably but axially fixedly mounted on the objective O of the microscope M.

Figure 2A:
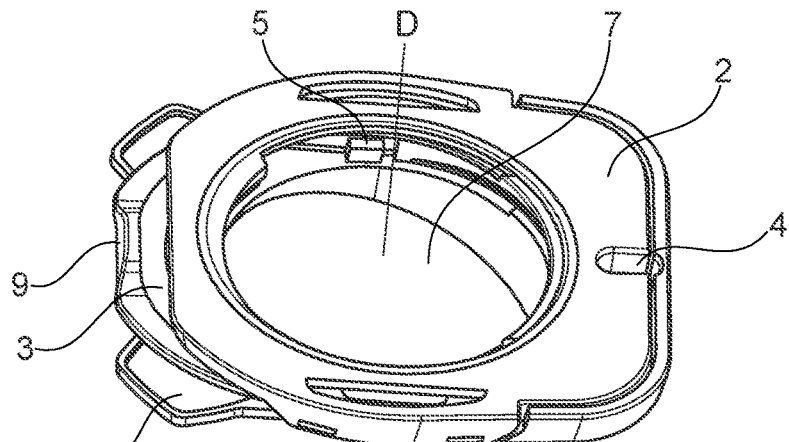
FIGS. 2a to 2c show different views of an adapter according to the invention in the open position.
Figure 2B:
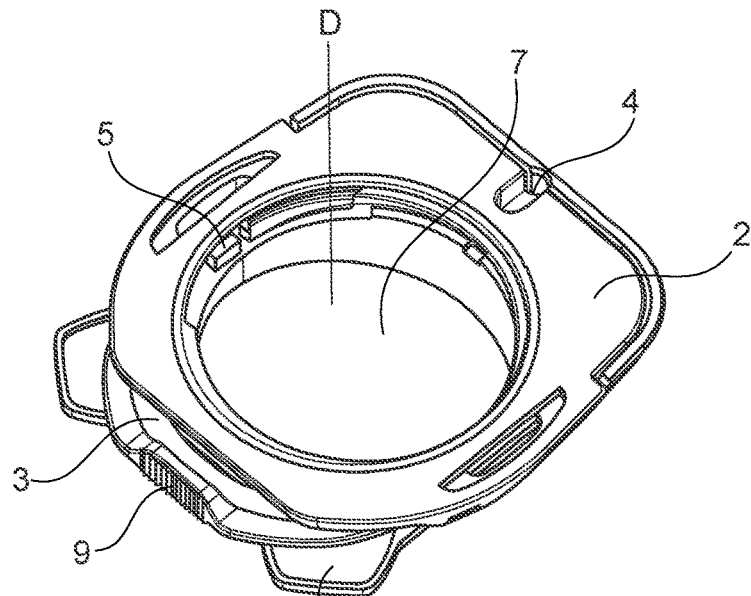
Figure 2C:
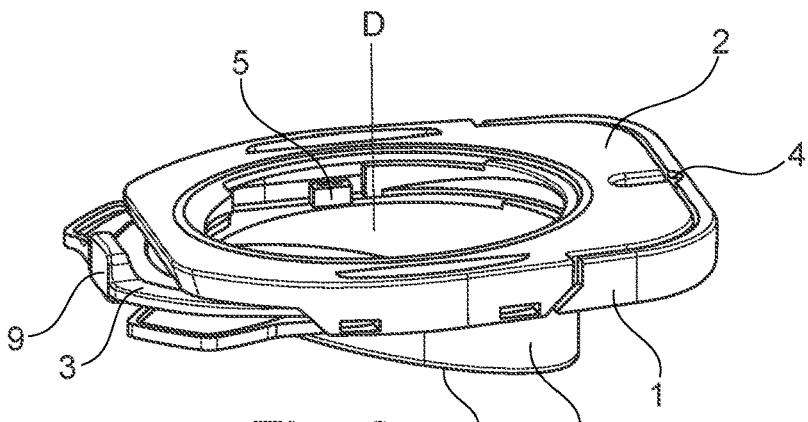

FIGS. 2a to 2c show different views of an adapter according to the invention in the open position.

FIGS. 2a to 2c show that the (slot-like) alignment receptacle 4 is formed coaxially to the passage D through the cap 2 and the base plate 1 together, i.e. jointly or cooperatively. Alternatively, however, it would also be possible to form the alignment receptacle only through the cap 2 or the base plate 1.

It is further preferable that the alignment receptacle 4 extends far enough into the body of the adapter axially parallel to the through opening D to ensure a secure receiving of a correspondingly shaped engaging portion, such as the alignment pin or alignment post A of the objective O of the microscope M. For example, in the shown embodiment the alignment receptacle 4 extends from the upper surface of the cap 2 to the surface of the circumferential flange 8 of the base plate 1 facing the cap 2. This depth ensures that the alignment pin A can be securely engaged with the alignment receptacle 4 and, for example, cannot slip out of the alignment receptacle 4 in an uncontrolled manner. Preferably, the gripping portion is configured and/or arranged in such a way, in particular the alignment pin is configured to have such a length that, while the adapter is incorrectly oriented, it keeps the adapter at such an axial distance from the latching geometry on the objective so that locking/latching of the movable body on the objective is not possible or at least considerably more difficult. Thus, the adapter can only be fixed or held in one (single) predetermined mounting position on the objective.

At this position it should be noted that the adapter and the gripping portion/alignment pin can be separate components or components that can be sold separately, which in this case together/in their cooperation form a positioning system. However, it is also possible to use corresponding, already existing geometries on a microscope/objective as gripping portion and to configure and place the positioning geometry/alignment pin accordingly.

In addition, as shown for example in FIG. 2b, the operating portion 9 of the movable element 3 may be further optimized for handling by the user, for example by modifying the surface of the operating portion 9 to ensure improved haptics or by applying a similar geometry to the cylindrical portion of component 2 or a similar surface forming the support for the other fingers.

As shown in FIG. 2b, for example, grooves, notches and/or preferably rib-like projections may be provided on the operating portion 9 to ensure a secure grip.

Figure 3A:
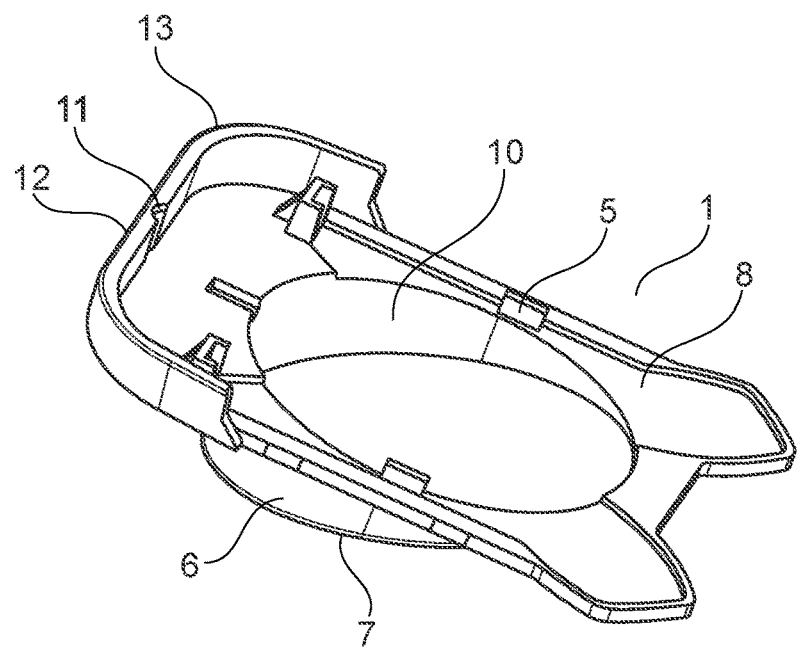
FIGS. 3a and 3b show a base plate of an adaptor according to the invention.
Figure 3B:
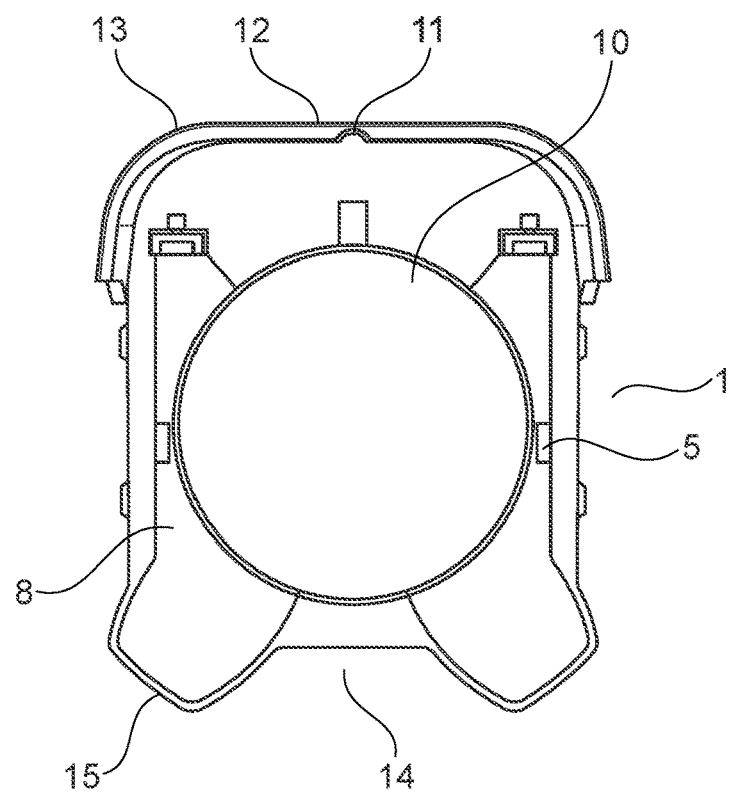

FIGS. 3a and 3b show a base plate 1 of an adapter according to the invention in detail.

As described above, the base plate 1 has the cylindrical body/socket 6 which has the optically transparent element (drape-lens) 7 at its one (lower) end, i.e. the drape-lens or the window 7, through which the image recording and lighting of the operating field by a microscope takes place when the adapter is mounted on the objective of the microscope and has the flange/collar 8 surrounding the opening 10 of the cylindrical base body 6 at its other (upper) end.

Figure 7:
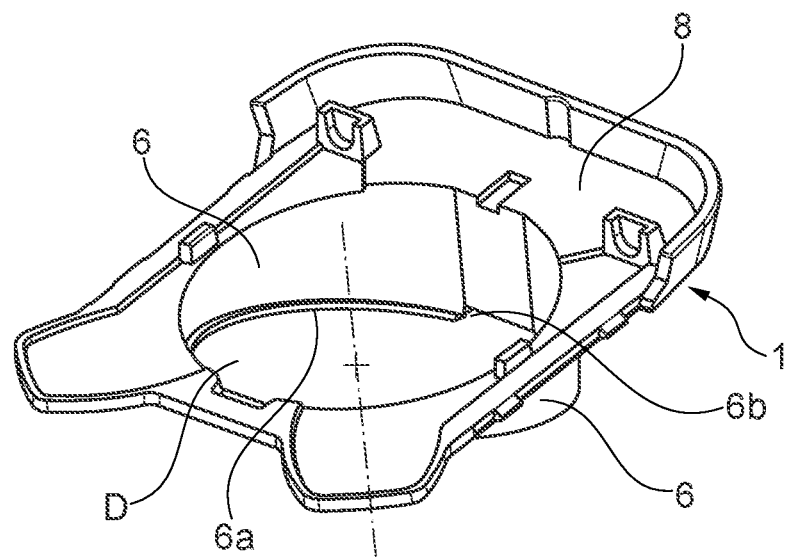
FIG. 7 shows a base plate for a loose inserting of a drape-objective and subsequent tensioning by means of a cap.
Figure 8:
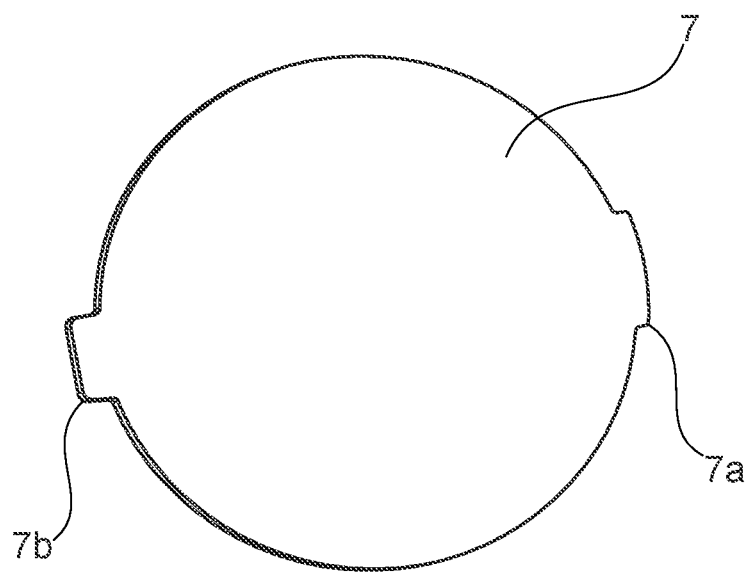
FIG. 8 shows a drape-objective for a loose inserting into the base plate according to FIG. 7.

As an alternative to this embodiment, FIGS. 7 and 8 show a multi-section construction of base plate 1 and drape-lens 7, i.e. a separation/division of the base plate 1 into a separate disc/drape-lens 7 with the window function, the base plate 1 with socket 6 and collar 8 and a holder which braces the drape-lens to the base plate 1. The holder can be formed by the cap 2 according to the above embodiment or by a further additional intermediate component (not shown).

In concrete terms, the separate drape-lens 7 has a circular window portion with a diameter roughly corresponding to the inner diameter of the socket, on the outer circumference of which two diametrically arranged lugs 7a, 7b are formed which extend radially outwards. The socket 6 of the base plate 1, at its one (lower) end/end portion, forms a radially inward projection/circumferential ring 6a which serves as a support for the separate drape-lens 7 and is aligned at an angle of inclination with respect to the collar/flange 8 or with respect to the socket axis indicated in FIG. 7, as defined above. In addition, a cutout 6b is formed on the socket wall directly above the inward projection/circumferential ring 6a as well as on a circumferential portion of the socket 6 axially furthest from the collar/flange 8 which is dimensioned in such a way that one of the lugs 7a on the drape-lens 7 can be inserted therein when the drape-lens 7 rests on the inward projection/circumferential ring. The diametrically opposed lug 7b is dimensioned so as to extend substantially to the upper side of the collar/flange 8, when the drape-lens 7 rests on the inward projection/circumferential ring 6a. If the cap 2 is then fitted on the upper side of the collar/flange 8 of the base plate 1 and fixed/clipped there, the cap 2 presses inevitably on the one upper lug 7b and thus tenses the drape-lens 7 between itself and the inward projection/circumferential ring 6a.

FIG. 3a further shows that, according to the present embodiment the base plate 1 has two limiting elements 5 or stoppers/projections, which are respectively provided on opposite sides of the opening 10 of the cylindrical body of the base plate 1 (diametrically opposed) and limit a movement of the movable element 3 from the open position to the locking position.

On the edge side 12 shown on the left in FIG. 3a, the base plate 1 has a section or a section area 11 of the alignment receptacle 4, which later interacts with a certain section area 16 of the cap 2 to form the alignment receptacle 4. Furthermore, a circumferential frame is formed on the edge side 12, which aligns itself perpendicular to the flange/collar and reinforces it. An internal recess, which extends coaxially to the socket and forms the one section/section area 11 of the alignment receptacle 4, is incorporated in the frame.

The area of the base plate 1 shown on the left in FIG. 3a, in which also the alignment receptacle 4 or at least the section or section area 11 of the alignment receptacle 4 formed by the base plate 1 is located, the edge side 12 forms a substantially straight edge portion with rounded corners 13, wherein during mounting the adapter on the microscope a user can apply his fingers (e.g. index finger, middle finger, ring finger) to the edge side 12 to provide therefore an abutment for exerting pressure on the operating portion 9 of the movable element 3 so as to bring or hold the adapter in the open position.

On the edge side 14 of the base plate 1 opposite to the edge side 12 with the section or section area 11 of the alignment receptacle 4, the base plate 1 can have lug-like projections 15 at corners, respectively, whereby the contour of the front side 14 defines a recess shape.

This makes it easier to apply pressure to the operating portion 9 of the movable element 3 which is positioned between the two lug-like projections 15.

FIG. 3b shows a top view of the base plate 1 shown in FIG. 3a. The same reference signs refer to the same elements or elements.

Figure 4A:
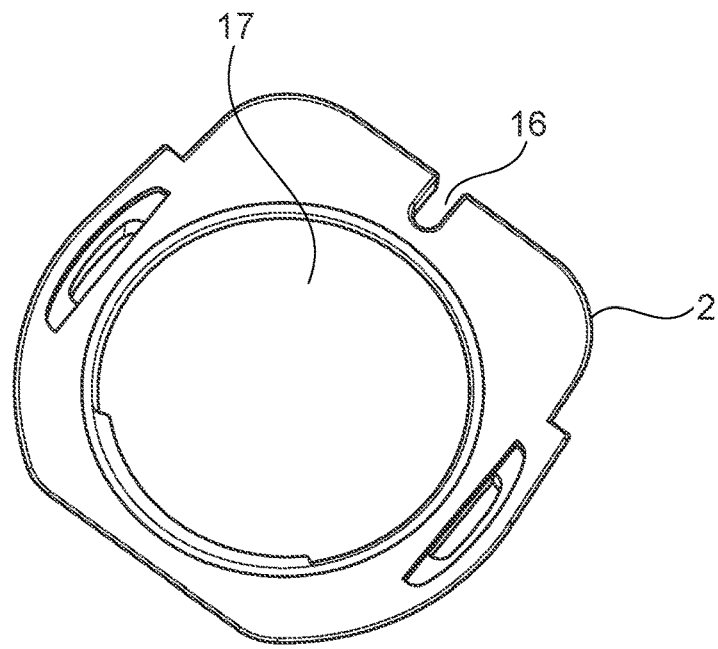
FIGS. 4a and 4b show a cap of an adaptor according to the invention.
Figure 4B:
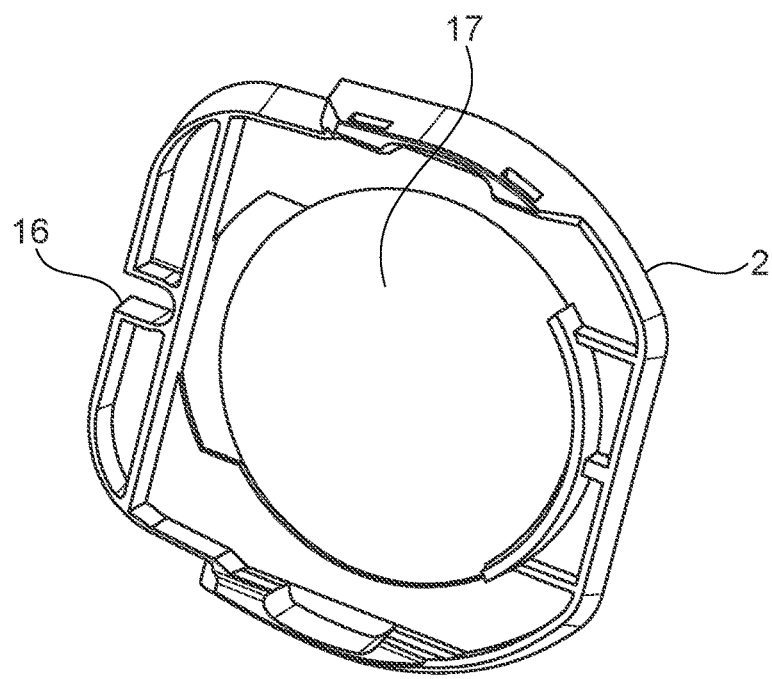

FIGS. 4a and 4b show the cap 2 of the adapter according to the invention in top view and in a view from below.

As can be seen in FIG. 4a, the cap 2 forms a section or section area 16 of the alignment receptacle 4. The section or section area 16 interacts with the section or section area 11 of the base plate 1 described above in such a way that these sections or section areas 11, 16 together form the alignment receptacle 4.

Figure 5A:
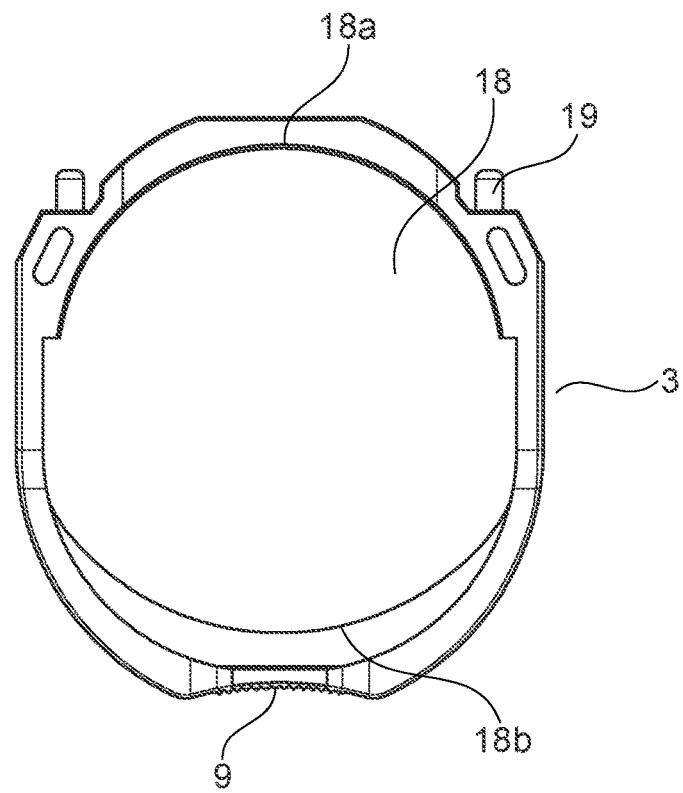
FIGS. 5a and 5b show a movable element of an adaptor according to the invention.
Figure 5B:
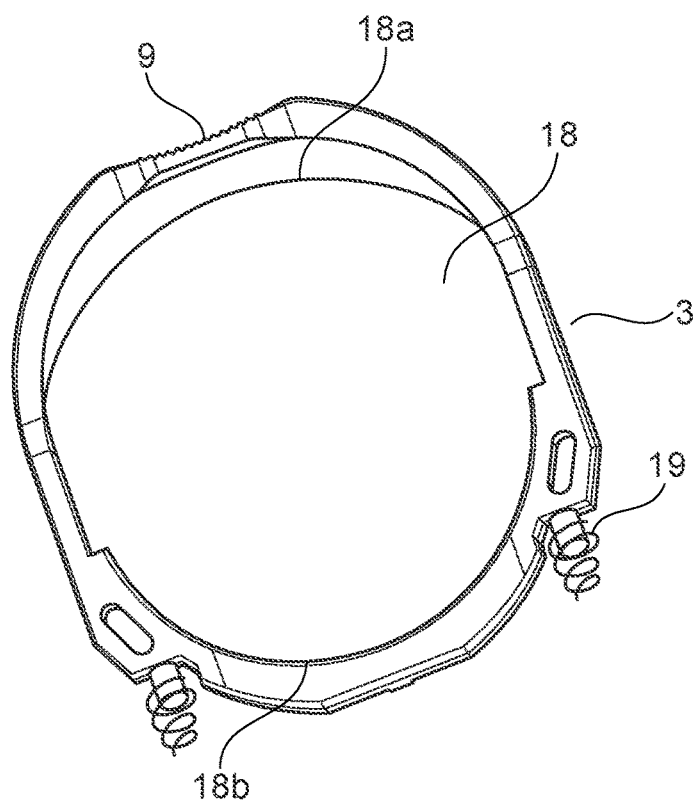

FIGS. 5a and 5b show the movable element (tongue plate) 3 of the adapter according to the invention.

The movable element 3 is a component which substantially has the shape of a ring/ring disk. In the movable element 3 shown in FIGS. 5a and 5b, the opening 18 or the diameter of the opening 18 of the movable element 3 is larger than the openings 10, 17 or the diameter of the openings 10, 17 of the cylindrical body/socket 6 of the base plate 1 and the cap 2 shown in FIGS. 3a, 3b, 4a and 4b.

In addition, FIGS. 5a and 5b show that the opening 18 of the movable element 3 is not exactly circular, but has curved portions 18a, 18b, each of which corresponds to a circular section (thus creating a kind of ellipse shape). As shown in FIGS. 5a and 5b, at least the circular portion 18b which determines the contour of the opening 18 of the movable element 3 on the side closest to the operating portion 9 is a circular portion of a circle whose radius is larger than the radius of the circle underlying the openings 10, 17 of the cylindrical body 6 of the base plate 1 and the cap 2.

In other words, the circular section 18b closest to the operating portion 9 of the movable element 3 which forms the contour of the opening 18 of the movable element 3 is less curved than the circle underlying the openings 10, 17 of the cylindrical body 6 of the base plate 1 and the cap 2.

In addition, as shown in FIGS. 5a and 5b, the movable element 3 has two retaining posts 19 extending in the element-plane direction for biasing elements, particularly in the form of coil springs or compression springs.

If the adapter according to the invention is assembled, or if the movable element 3 is placed or applied on the base plate 1, as shown for example in FIGS. 3a and 3b, the biasing elements/compression springs/coil springs are placed between the retaining posts 19 of the movable element 3 and corresponding counter bearings of the base plate 1 and/or the cap 2 in order to bias the movable element 3 in the locking position or locking status.

The present invention again relates, in summary, to a mounting adapter for the detachable attachment of a sterile cover on an objective of a microscope, with a passage D for the inserting of the objective therein, wherein a drape-lens or light-transparent disc 7 is arranged in the passage in such a way that it adopts an oblique angle to the longitudinal axis of the passage D and with a preferably manually operable latching device 3 for the axial holding of the mounting adapter on the objective inserted into the passage D. According to the invention, a positioning geometry 4 is provided which is configured and arranged to cause a reproducible target angular positioning or target rotational alignment of the mounting adapter on the objective preferably exclusively by its axial fitting and further preferably to fulfil its positioning function independently and separately from the latching device.

The invention claimed is:

1. A mounting adapter for detachably attaching a sterile cover to an objective of a microscope, the mounting adapter comprising:
   a passage for the insertion of the objective therein, in which a drape-lens or light transparent disc is arranged such that the drape-lens or light transparent disc adopts an oblique angle to a longitudinal axis of the passage;
   a latching device having a ring-shape for an axial holding of the mounting adapter on the objective inserted into the passage, the latching device including at least one retaining post that is placed through a middle of a biasing element, wherein the biasing element enables the latching device to be moved to an open position and return to a locking position to axially hold the mounting adapter on the objective; and
   an alignment receptacle configured and arranged to cause a reproducible target angular positioning and/or target rotational alignment of the mounting adapter on the objective exclusively by its axial fitting and further to fulfil its positioning function independently and separately from the latching device.

2. The mounting adapter according to claim 1, wherein the alignment receptacle is configured and/or arranged on the mounting adapter such that, when an actual angular position is unequal to the target angular position, the alignment receptacle is configured to prevent the objective from being inserted into the passage to such a target insertion depth at which the latching device causes the mounting adapter to be held axially on the objective.

3. The mounting adapter according to claim 1, wherein the alignment receptacle includes a clearance or a recess with an axially acting end stopper or a projection on the mounting adapter.

4. The mounting adapter according to claim 3, wherein the alignment receptacle is includes a blind hole which that coaxially extends in the mounting adapter.

5. The mounting adapter according to claim 1, further comprising a base plate comprising a socket forming a through opening, at one axial end portion of which the drape-lens or light transmissive disc is arranged, and the other axial end portion of which is surrounded by a flange, on a side facing away from the socket of which a cap with a through opening is fitted such that the through openings of the base plate and the cap are aligned, forming a common passage, and a receiving compartment is formed therebetween, in which a manually movable tongue plate is inserted for selectively narrowing the passage.

6. The mounting adapter according to claim 5, wherein the drape-lens or light transparent disc is configured as a component separate from the base plate and the cap and a radially inwardly projecting shoulder which forms an axial support for the drape-lens or light transparent disc is formed or arranged in the socket of the base plate.

7. The mounting adapter according to claim 6, wherein the cap has on its side facing the base plate a pressing portion that includes at least one of grooves, notches or rib-like projections.

8. The mounting adapter according to claim 7, wherein the socket is formed with a cutout or recess and the drape-lens or light transmissive disc has a radially projecting lug that is inserted into the cutout or recess for axially holding the drape-lens or light transmissive disc.

9. A microscope with an objective, which is configured for use with the mounting adapter according to claim 1, wherein the microscope has an engaging portion that is designed to be inserted into the alignment receptacle and which is provided and configured to determine, in cooperation with the alignment receptacle, at least one specific target angular position of the mounting adapter and further a specific target axial position of the mounting adapter on the objective.

10. A system comprising the mounting adapter according to claim 1, and a microscope with an objective, which is configured for use with the mounting adapter, wherein the microscope has an engaging portion coaxially to an objective extending alignment pin that is configured to be inserted into the alignment receptacle of the mounting adapter and which is provided and configured to determine, in cooperation with the alignment receptacle, at least one specific target angular position of the mounting adapter and further a specific target axial position of the mounting adapter on the objective.

* * * * *